United States Patent
Sampson

(10) Patent No.: US 6,238,925 B1
(45) Date of Patent: May 29, 2001

(54) METHOD FOR DETERMINING LIKELIHOOD OF DEVELOPING CLINICAL TOLERANCE

(75) Inventor: Hugh A. Sampson, Larchmont, NY (US)

(73) Assignee: Panacea Pharmaceuticals, LLC, Fairfield, CT (US)

(*) Notice: Subject to any disclaimer, the term of this patent is extended or adjusted under 35 U.S.C. 154(b) by 0 days.

(21) Appl. No.: 09/238,448

(22) Filed: Jan. 28, 1999

Related U.S. Application Data

(60) Provisional application No. 60/073,171, filed on Jan. 30, 1998.

(51) Int. Cl.$^7$ .................................................. G01W 33/06

(52) U.S. Cl. ............................ 436/23; 436/22; 436/21; 436/20; 436/543; 435/7.1; 435/4; 424/185.1; 424/184.1

(58) Field of Search ..................... 435/7.1, 4; 424/185.1, 424/184.1; 436/23, 22, 21, 20, 543

(56) References Cited

U.S. PATENT DOCUMENTS

| | | | |
|---|---|---|---|
| 5,480,972 | * 1/1996 | Avjioglu et al. ..................... | 530/379 |
| 5,558,869 | * 9/1996 | Bworks, Jr. et al. ............. | 424/276.1 |
| 5,869,333 | * 2/1999 | Singh et al. ......................... | 435/325 |
| 5,939,283 | * 8/1999 | Morgenstern et al. ............. | 435/69.1 |

FOREIGN PATENT DOCUMENTS

WO 95/17677  6/1995 (WO).

OTHER PUBLICATIONS

Ball, et al., "Isolation of an immunodominant IgE hapten from an epitope expression cDNA library. Dissection of the allergic effector reaction," *J Biol Chem* 269:28323–8 (1994).

Bernhisel–Broadbent, et al., "Allergenicity and antigenicity of chicken egg ovomucoid (Gal d III) compared with ovalbumin (Gal d I) in children with egg allergy and in mice," *J Allergy Clin Immunol* 93:1047–1059 (1994).

Bernhisel–Broadbent, et al., "Cross–allergenicity in the legume botanical family in children with food hypersensitivity. II. Laboratory correlates" *J Allergy Clin. Immunol.* 84:701–709 (1989).

Bock & Atkins, "The Natural history of peanut allergy," *J. Allergy Clin. Immunol* 83: 900–904 (1989).

Bock, "Prospective appraisal of complaints of adverse reactions to foods in children during the first 3 years of life," *Pediatrics* 79:683–688 (1987).

Bock, "The natural history of food sensitivity," *J Allergy Clin Immunol* 69:173–17 (1982).

Bresson, et al., "Microvillus membrane differentiation: quantitative difference in cholera toxin binding to the intestinal surface of newborn and adult rabbits," *Pediatr Res* 18:984–987 (1984).

Brunner & Walzer, "Absorption of undigested proteins in human beings," *Arch Intern Med* 42:173–179 (1928).

Cooke & Sampson, "Allergenic properties of ovomucoid in man," *J. Immunol.* 159:2026–2032 (1997).

Halken, et al., "Effect of an allergy prevention programme on incidence of atopic symptoms in infancy. A prospective study of 159 "high–risk" infants," *Allergy* 47:545–553 (1992).

Host, "Cow's milk protein allergy and intolerance in infancy. Some clinical, epidemiological and immunological aspects," *Pediatr Allergy Immunol* 5(5 Suppl):1–36 (1994).

Husby, et al., "Passage of undergraded dietary antigen into the blood of healthy adults. Quantification, estimation of size distribution, and relation of uptake to levels of specific antibodies," *Scand J Immunol* 22:83–92 (1985).

Hyman, et al., "Gastric acid secretory function in preterm infants," *J Pediatr* 106:467–471 (1985).

James, et al., "An overview of food hypersensitivity," *Pediatr Allergy Immunol* 3:67–78 (1992).

Johansson, et al., The relevance of anti–food antibodies for the diagnosis of food allergy, *Ann Allergy* 53:665–672 (1984).

Kato, et al., "Chicken ovomucoid: determination of its amino acid sequence, determination of the trypsin reactive site, and preparation of all three of its domains," *Biochemistry* 26:193–201 (1987).

(List continued on next page.)

Primary Examiner—T. Wessendorf
(74) *Attorney, Agent, or Firm*—Arnall Golden & Gregory, LLP

(57) ABSTRACT

It has been discovered that one can predict the likelihood a child will outgrow an allergy, especially a food allergy, by screening for IgE antibodies immunoreactivities with linear versus conformational epitopes. The child is first screened using standard techniques to determine what antigens the child is allergic to. The immunoglobulins in the sample from the patient are then characterized either using the natural purified antigen, recombinant antigen, reduced and alkylated antigen, proteolytic fragments of the antigen or synthetic peptides of between four and 40 amino acids in length, preferably six to ten amino acids, which can be immobilized for rapid and accurate screening. The antibodies from the patient, typically present in a serum or plasma sample, are reacted with the protein or peptides to determine which peptides are bound by the antibodies. These antibodies are then characterized to determine if the epitopes they bind are linear or conformational. Those patients having antibodies primarily reactive with conformational epitopes (that is, reactive with native protein or proteolytic fragments, as compared to reduced and alkylated protein or synthetic linear peptides) will typically outgrow their allergies. Those that are reactive primarily with linear epitopes may need to be treated to induce tolerance. A similar method for evaluation of IgG antibodies can be used to predict the prognosis of certain inflammatory disorders, especially those involving the gastrointestinal tract.

5 Claims, 6 Drawing Sheets

OTHER PUBLICATIONS

Kletter, et al., "Immune responses of normal infants to cow milk. I. Antibody type and kinetics of production," *Int Arch Allergy Appl Immunol* 40:656–666 (1971).

Laffer, et al., "Molecular characterization of Bip 1, a monoclonal antibody that modulates IgE binding to birch pollen allergen, Bet v 1," *J Immunol* 157:4953–4962 (1996).

Lebenthal, et al., "Development of functional responses in human exocrine pancreas," *Pediatrics* 66:556–560 (1980).

May, et al., "A study of serum antibodies to isolated milk proteins and ovalbumin in infants and children," *Clin Allergy* 7:583–595 (1977).

Pastorello, et al., "Role of the elimination diet in adults with food allergy," *J Allergy Clin Immunol* 84:475–483 (1989).

Sampson & McCaskill, "Food hypersensitivity and atopic dermatitis: evaluation of 113 patients," *J Pediatr* 107:669–675 (1985).

Sampson & Scanlon, "Natural history of food hypersensitivity in children with atopic dermatitis," *J Pediatr* 115:23–27 (1989).

Sampson, "Food sensitivity and the pathogenesis of atopic dermatitis," *J R Soc Med.* 90(suppl 30):3–9 (1997).

Sampson, "The immunopathogenic role of food hypersensitivity in atopic dermatitis," *Acta Derm Veneorol (Stockh)* Suppl. 176:34–37 (1992).

Savilhati, et al., "Prolonged exclusive breast–feeding results in low serum concentrations of immunoglobulin G, A and M," *Acta Paediatr Scand* 76:1–6 (1987).

Shub, et al. "Age–related changes in chemical composition and physical properties of mucus glycoproteins from rat small intestine," *Biochem J* 215:405–411 (1983).

Stanley, et al., "Identification and mutational analysis of the immunodominant IgE binding epitopes of the major peanut allergen *Ara h 2*," *Arch Biochem. & Biophysic.* 342:244–253 (1997).

Stanley, et al., "Identification and mutational analysis of the immunodominant IgE binding epitopes of the major peanut allergen *Ara h 2*," *Biological Abstracts*, Abstract No. PREV199799604539.

Wilson, et al., "Absorption of undigested proteins in human beings," *Am J Dis Child* 50:49–54 (1935).

Zeiger, et al., "Effect of combined maternal and infant food–allergen avoidance on development of atopy in early infancy: a randomized study," *J Allergy Clin Immunol* 84:72–89 (1989).

Adams et al, Immunology, Cell Biology, 69, (1991), pp. 191–197.*

The Merck Manual, 11th ed. (1966), pp. 578–579.*

D'Abusco et al, Clinical & Expt'l. Allergy, 26, (1996), pp. 223–231.*

Matsuda et al, J. Biochem., 100, (1986), pp. 985–988.*

Ball et al, Clin. & Expt'l. Allergy, 24, (1994), pp. 758–764.*

Hunt, Biochemical Society Transactions, (1997), p. 25.*

* cited by examiner

METHOD FOR DETERMINING LIKELIHOOD OF DEVELOPING CLINICAL TOLERANCE

This application claims priority to U.S. Ser. No. 60/073,171 filed Jan. 30, 1998.

The United States government has certain rights in this invention by virtue of grants AI24439 from the NIAID and RR00052 from the DRR, National Institutes of Health.

BACKGROUND OF THE INVENTION

Hypersensitivity reactions to foods affect up to 6% of children in the first few years of life (Bock, S. A. 1987. *Pediatrics* 79:683–688), with milk, egg, and peanut accounting for most of the documented allergic responses (James J M and Sampson H A. 1992. *Pediatr Allergy & Immunol* 3:67–78). Most milk-allergic children develop cow milk hypersensitivity in the first year of life and then approximately 80% "outgrow" their reactivity (i.e. become clinically tolerant) by three years of age (Host, A. 1994. *Pediatr Allergy Immunol* 5:5–36). Hypersensitivity to hen's egg and peanut are more often recognized in the second year of life. Egg allergy appears to be more persistent than cow milk allergy whereas peanut allergy is very rarely "outgrown" (Bock, S. A. 1982. *J Allergy Clin Immunol* 69:173–177; Sampson, H. A. and S. M. Scanlon. 1989. *J Pediatr* 115:23–27; Bock, S. A. and F. M. Atkins. 1989. *J Allergy Clin Immunol* 83:900–904). The basis for these differences in persistence of clinical hypersensitivity to different food allergens is unknown.

Egg allergy is present in nearly two-thirds of children with atopic dermatitis (Sampson, H. A. J. 1997 *Roy. Soc. Med.* 90(suppl 30):3–9). When egg allergic children are placed on a diet devoid of all egg protein, about one-third develop clinical tolerance to egg within 2 years, even though IgE antibodies to egg (e.g. positive prick skin tests) persist for several years (Sampson 1989). Ovomucoid (Gal d 1) is the dominant allergen in hen's egg, and children with persistent egg allergy have significantly higher concentrations of IgE anti-ovomucoid antibodies than those who "outgrow" their reactivity (Bernhisel-Broadbent, J.,et al. 1994. *J Allergy Clin Immunol* 93:1047–1059). Ovomucoid is a glycoprotein comprised of 186 amino acids arranged in three tandem domains containing nine intra-domain disulfide bonds and five carbohydrate side chains (Kato, et al. 1987. *Biochemistry* 26:193–201).

It is an object of this invention to provide an assay including methods and reagents for predicting the likelihood that children will outgrow an allergy, especially a food allergy.

It is a further object of the present invention to provide a method and reagents to screen for the presence of antibodies to linear versus conformational epitopes in patient samples.

SUMMARY OF THE INVENTION

Methods and reagents are provided for use in predicting the likelihood a child will outgrow an allergy, especially a food allergy, by screening for the immunoreactivity of IgE antibodies with linear epitopes as compared to conformational epitopes. The child is first screened using standard techniques to determine what antigens the child is allergic to. The immunoglobulins in the sample from the patient are then characterized either using the natural purified antigen, recombinant antigen, reduced and alkylated antigen, proteolytic fragments of the antigen or synthetic peptides of between four and 40 amino acids in length, preferably six to ten amino acids, which can be immobilized for rapid and accurate screening. The antibodies from the patient, typically present in a serum or plasma sample, are reacted with the protein or peptides to determine which peptides are bound by the antibodies. These antibodies are then characterized to determine if the epitopes they bind are linear or conformational. Those patients having antibodies primarily reactive with conformational epitopes (that is, reactive with native protein or proteolytic fragments, as compared to reduced and alkylated protein or synthetic linear peptides) will typically outgrow their allergies. Those that are reactive primarily with linear epitopes may not outgrow their reactivity and may need to be treated to induce tolerance.

The method for screening is demonstrated in an example utilizing pooled sera from egg-allergic patients and overlapping synthetic decapeptides derived from the sequence for ovomucoid. Ovomucoid was found to possess five allergenic IgE-binding epitopes. Evaluating allergenic epitopes with individual patient sera revealed three patterns of epitope binding: extensive IgE binding to decapeptides in all three ovomucoid domains, IgE binding predominantly to peptides in the first domain, and virtually no IgE binding to any synthetic peptides, indicating that most IgE antibodies in the latter group recognized conformational epitopes. All patients had extensive IgG antibody binding to the linear, synthetic peptides whereas all non-egg allergic controls recognized only conformational epitopes. Patients in the group with extensive IgE binding to linear decapeptides tended to be older and have more severe, generalized allergic symptoms following egg ingestion than the patient group with little IgE antibody to synthetic peptides. These findings indicate that differential antigen processing and antibody-epitope structural recognition play a role in the clinical course of allergen sensitivity.

A similar method for evaluation of IgG antibodies can be used to predict the prognosis of certain inflammatory disorders, especially those involving the gastrointestinal tract such as Crohn's disease, ulcerative colitis, and celiac disease.

BRIEF DESCRIPTION OF THE DRAWINGS

FIG. 3a, possessed IgE antibodies to epitopes in all three ovomucoid domains, Group 2, FIG. 3b, had ovomucoid-specific IgE antibodies primarily to epitopes in the first ovomucoid domain, and Group 3, FIG. 3c, had negligible IgE antibodies to any synthetic decapeptides.

DETAILED DESCRIPTION OF THE INVENTION

In the generation of IgE-specific antibodies, B cells are activated following surface-IgM binding to exposed oligopeptides on the native protein. Consequent IgE antibodies produced may be directed at linear epitopes which represent 8–20 consecutive (sequential) amino acids or conformational epitopes which are comprised of amino acid residues from different regions of the allergen. Both linear (e.g. Phl p 1; timothy grass (Ball, et al. 1994. *J Biol Chem* 269:28232–28242)) and conformational (Bet v 1; birch pollen (Laffer, et al. 1996. *J Immunol* 157:4953–4962)) B cell epitopes have been defined to inhaled aeroallergens, although the latter are presumed to predominate. Since food allergens are subjected to extensive chemical and proteolytic digestion prior to absorption and uptake by cells of the gut-associated lymphoid tissue, it has been inferred that food allergenic epitopes are predominantly linear in nature. However, in a previous study utilizing pooled sera from egg allergic patients, 5 IgE- and 7 IgG-antibody binding sites were identified along the 186 amino acid residues comprising ovomucoid (Cooke and Sampson *J Immunol.* 1997 159, 2026–2032). Evaluation of reduced and alkylated, i.e. "linearized," ovomucoid suggested that not all patients had anti-ovomucoid antibodies that recognized linear epitopes.

Figure 3A:
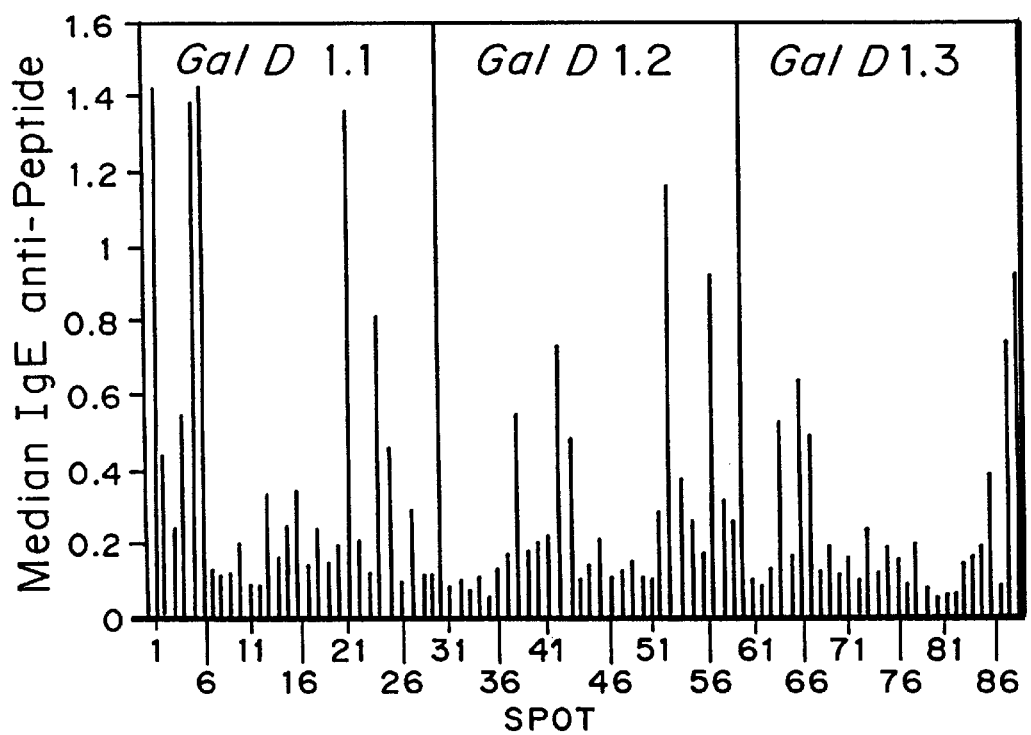
FIGS. 3a–c. Patterns of ovomucoid-specific IgE binding to synthesized decapeptides, shown as median cumulative SPOTs IgE Gal d 1 OD scores: Group 1.
Figure 3B:
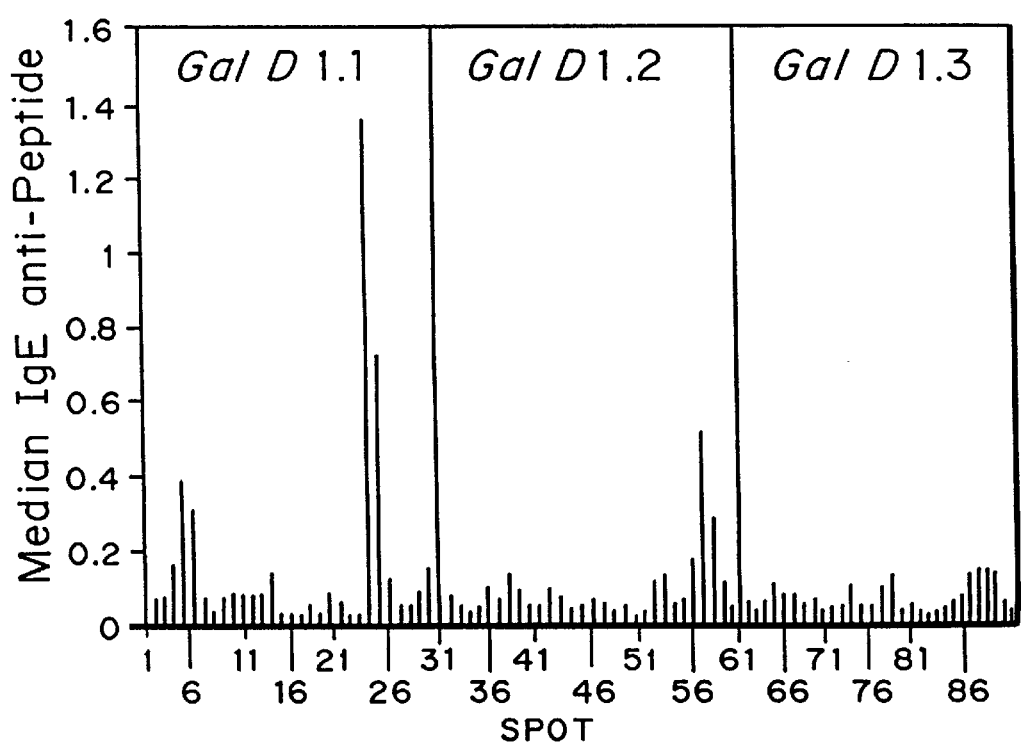
Figure 3C:
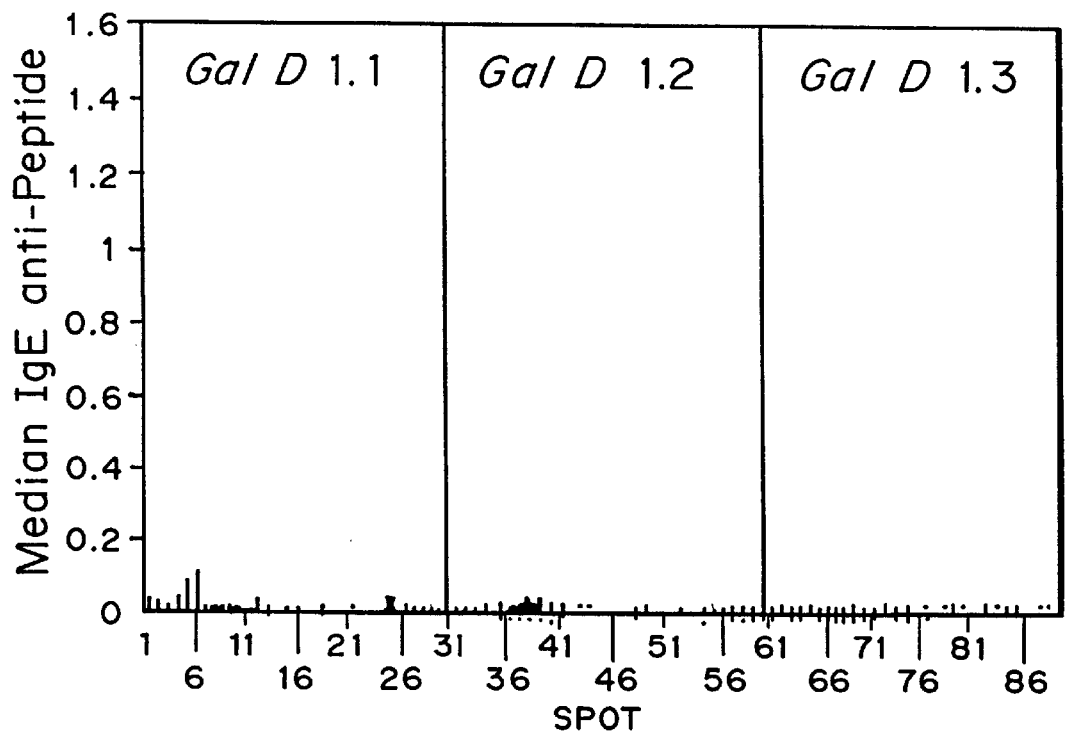

In the following example, overlapping, linear decapeptides and linearized (reduced and alkylated) whole ovomucoid were utilized to compare individual patient's IgE antibody recognition of linear ovomucoid epitopes. Sera were selected from 17 egg allergic children with relatively high levels of egg-specific IgE antibodies (greater than or equal to 35 kUA/L) for screening ovomucoid epitopes. When IgE binding to the synthesized decapeptides were compared, it appeared that there were three different patterns of antibody binding. As depicted in FIGS. 3a–3c, one patient group's IgE antibodies recognized most of the ovomucoid allergenic epitopes previously identified (Cooke and Sampson 1997), one group's IgE recognized allergenic epitopes primarily in the first ovomucoid domain, and the third group had virtually no IgE binding to any of the synthesized decapeptides. In the egg-allergic patients studied, three patterns of ovomucoid-specific IgE binding were seen to the synthesized decapeptides. As reflected in the median cumulative SPOTs IgE Gal d 1 OD scores, one group of patients (Group 1; FIG. 3a) possessed IgE antibodies to epitopes in all three ovomucoid domains, one group had ovomucoid-specific IgE antibodies primarily to epitopes in the first ovomucoid domain (Group 2; FIG. 3b), and one group had negligible IgE antibodies to any synthetic decapeptides (Group 3; FIG. 3c).

Figure 5A:
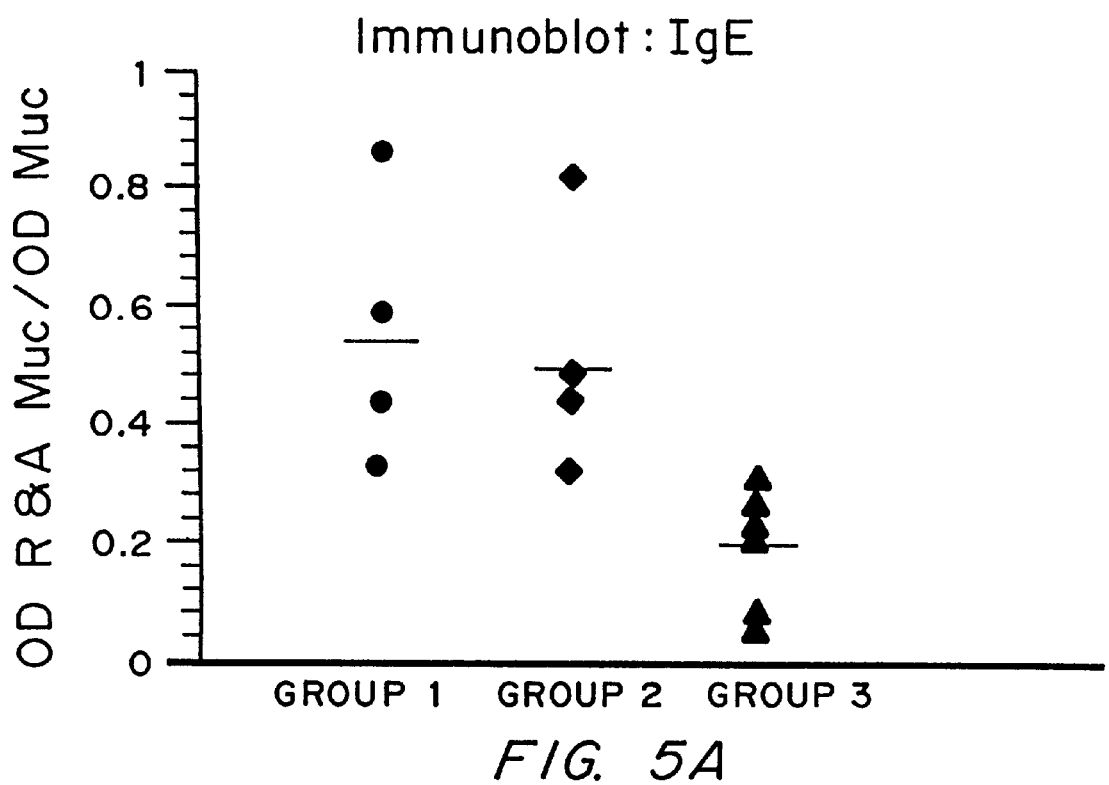
FIGS. 5a–b. The ratio of ovomucoid-specific IgE (FIG. 5a) and IgG (FIG. 5b) antibodies to native and "linearized" (reduced and alkylated) ovomucoid were compared for each egg allergic patient group.

Since the quantities of egg-specific IgE antibodies were similar in the three groups, this suggested that the third group of patients possessed ovomucoid-specific IgE antibodies that recognized primarily conformational epitopes. This supposition was supported by findings comparing the binding of patients' ovomucoid-specific IgE to "native" and "linearized" (reduced and alkylated) ovomucoid (FIG. 5a). While ovomucoid-specific IgE antibody binding to native ovomucoid was similar in the 3 patient groups, only about 22% of the third groups' ovomucoid-specific IgE bound linearized ovomucoid compared to the native form whereas greater than 50% of the first groups' ovomucoid-specific IgE bound the linearized form of ovomucoid.

These studies have led to the development of a method and assay kit for the determination of the liklihood any particular individual will "outgrow" an allergy, especially a food allergy.

Assay for Determining the Liklihood of Outgrowing an Allergy

Method

The method is based on the discovery that children are more likely to become tolerant to, or "outgrow" allergies to conformational epitopes as compared to linear epitopes. Therefore, the test will typically be performed using samples, using a blood or serum sample, most preferably children, although individuals of any age can be tested. These individuals are first identified by screening for allergies using standard tests, for example, by injection of one or more antigens at different titers to determine if the individual is allergic to the antigen and the extent to which the individual is allergic. Antibodies are typically obtained by drawing a sample of the patient's blood, then removing the red cells and testing the remaining serum or plasma. The samples can be screened directly for reactivity of the IgE with defined epitopes presented by the antigen (Cooke and Sampson 1997) or the IgE antibodies separated out from the other antibodies using methods known to those skilled in the art and screened for reactivity. Optionally, the sample can also be screened for IgG reactive with the epitopes.

Although all egg-allergic patients in the study described in the example developed their egg hypersensitivity in the first two years of life, the first patient group was older and had more pronounced allergic reactions following the ingestion of egg than the third patient group. The first patient group's extensive ovomucoid-specific IgE antibody binding to numerous linear allergenic epitopes is similar to that seen in peanut-allergic patients to Ara h 1 and Ara h 2, major peanut allergens (Stanley, et al. 1997. *Arch. Biochem. & Biophysic.* 342, 244–253). Patients with peanut allergy tend to have "protracted" (life-long) reactivity to peanut (Bock and Atkins 1989), suggesting the possibility that "protracted" food hypersensitivity is associated with the development of significant quantities of IgE antibodies to linear epitopes. Of note, a 32 year old egg allergic individual who has experienced repeated anaphylactic reactions to egg has ovomucoid-specific IgE antibodies with extensive binding to the linear decapeptides, as seen in the first group of patients in this study.

The example supports the association between IgE binding to epitope structure, i.e. linear versus conformational, and the development of "protracted" food hypersensitivity. Infants have been shown to have increased levels of food proteins in the circulation following meals, felt to be secondary to maturational delay in the development of digestive processes, e.g. stomach acidity, proteolytic enzyme activity, mucin composition, etc., and increased antigen uptake (Hyman, et al. 1985. *J Pediatr* 106:467–471; Lebenthal, E. and P. C. Lee. 1980. *Pediatrics* 66:556–560; Shub,et al. 1983. *Biochem J* 215:405–411; Bresson, et al. 1984. *Pediatr Res* 18:984–987). The "leaky" infant gut would allow significant quantities of conformational intact food proteins to gain access to local B cells that upon activation generate ovomucoid-specific IgE antibodies in genetically predisposed hosts. With maturation of the gastrointestinal tract, less conformational intact protein would be accessible to activate gut-associated lymphoid tissue and IgE-bearing tissue mast cells, resulting in loss of clinical reactivity and eventual loss of allergen-specific IgE antibody synthesis. Complete dietary exclusion of egg protein would further promote loss of clinical reactivity, whereas continued exposure to minute amounts of egg protein could result in the development of IgE antibodies to linear ovomucoid epitopes and protracted reactivity. In the mature gut, minute quantities of immunologically intact proteins (probably linear epitopes) penetrate the gastrointestinal barrier (Host 1994; Brunner, M and Walzer M. 1928. *Arch Intern Med* 42:173–179; Wilson S J and Walzer M. 1935. *Am J Dis Child* 50:49–54; Husby, et al. 1985. *Scand J Immunol* 22:83–92). This is consistent with the observation that the likelihood of losing clinical reactivity is associated with the age of the patient at the time of diagnosis, the degree of avoidance of the responsible allergen, and the allergen in question (peanut, tree nut and seafood allergies are rarely "outgrown"). Younger children produce confrontational ISA. The younger the patient at the time food sensitivity is diagnosed and/or the more stringent the allergen avoidance, the more likely the patient will "outgrow" his/her food allergy (Bock 1982; Sampson and Scanlon 1989; Pastorello, et al 1989. *J Allergy Clin Immunol* 84:475–483).

Allergens

Any antigen can be used for screening as described herein. The most typical antigens will be food allergens, such as egg, tree nut, peanut, and milk. Other common allergens include pollens, dust, mold, and mildew, as well as insect, domestic animal (dog, cat, bird), and plant allergens.

To test for reactivity with conformational epitopes, the allergens can be utilized as the intact protein, recombinant protein, or proteolytic fragments. The properties of the allergen can be modified by selection of the expression host—for example, bacterial expression systems do not typically glycosylate proteins, yeast and baculovirus/insect systems yield modified glycosylation, and even within eukaryotic expression systems, there can be modifications in glycosylation and phosphorylation, to alter reactivity and further characterize the epitope.

Linear epitopes can be short proteolytic fragments or peptides made by expression of recombinant DNA or synthetically using standard technology. The peptides will typically be from four to forty amino acids in length, more preferably from six to twenty, most preferably eight. These are designed based on the known amino acid sequence, usually available through a public source such as GenBank. The peptides are synthesized in the preferred embodiment beginning at one through nine amino acid residues, two through ten, and so on to the end of the protein.

The allergen or portion thereof to be tested for binding is preferably immobilized, for example, in a 96 well plate or on a piece of chromatographic paper, and then tested for binding as described in the example. The allergen can be bound to a particle or other known means for solution phase testing, or testing in an ELISA or using a fluorometric technique.

Kits

The method is preferably performed using kits containing the reagents for identifying the IgE antibodies in a patient sample reactive with sufficient linear and conformational epitopes to characterize the patient's prognosis. A typical kit will include a multiwell device having immobilized therein either linear or conformational epitopes to one or more allergens. The kit will also include reagents for detection or separation of IgE from IgG, such as fluorescent labelled immunoglobulin which are specific to IgE, and buffers for washing off unbound materials. The kit can be used to determine the relative amounts of IgE to linear versus conformational antibody by assessing reactivity at different titers to one or more linear epitopes and to one or more conformational epitopes, then determining their relative proportions.

The result of the test is typically a ratio of the proportion of IgE reactive with linear versus conformational epitopes, without reference to a negative or positive control, although it may be desirable to include positive and negative IgE samples reactive with either linear or conformational epitopes to insure the integrity of the test kit reagents and assay conditions.

Methods for Treatment of Allergies, especially Food Allergies

Those individuals having primarily IgE reactive with conformational epitopes are more likely to outgrow the allergy than those characterized principally by reactivity with linear epitopes. This is further demonstrated by the examples. In infants predisposed to atopy, the development of IgE antibodies to conformational versus linear epitopes may in part reflect maturational delay and/or molecular differences in antigen-processing by the gastrointestinal tract, immaturity of the gut, and allergen exposure. Studies on the prevention of allergy in infants at "high risk" for developing atopy have shown that complete avoidance of cow milk (a major food allergen) for at least the first year of life results in less milk allergy compared to infants placed on no dietary restriction (Zeiger,et al. 1989. *J Allergy Clin Immunol* 84:72–89; Halken, et al. 1992. *Allergy* 47:545–553.).

Based on the above information, one is able to develop generalized screening methods and formulations for screening, to aid in the decision whether or not a patient should undergo an immunotherapeutic modality to induce tolerance in allergic patients. Immunotherapeutic modalities that may be prescribed based on the results of the screening include complete avoidance of the allergen, for example, the food that contains the epitopes reactive with the patient IgE, or desensitization therapy, typically injections of increasing amounts of antigen over time to induce production of IgG antibodies which bind to the epitopes, blocking binding to IgE, which results in the immune response, following crosslinking of the IgE and degranulation of mast cells.

Method for Assessing Prognosis in Inflammatory Disorders

IgG antibodies to food proteins can be detected in virtually all individuals exposed to food antigens (Johansson,et al. *Ann Allergy* 53:665–672; Savilhati, et al. 1987. *Acta Paediatr Scand* 76:1–6) although levels of IgG food-specific antibodies tend to decrease with age (Kletter, et al. 1971. *Int Arch Allergy Appl Immunol* 40:656–666). Patients with food allergies or inflammatory bowel disorders (e.g. celiac disease, inflammatory bowel disease, etc.) tend to have markedly elevated levels of food-specific IgG ( May,et al. 1977. *Clin Allergy* 7:583–595).

The example demonstrates that patients with protracted egg allergy possess large quantities of IgE antibodies that bind linear ovomucoid epitopes whereas younger patients possess primarily IgE antibodies that bind conformational epitopes. In addition, egg allergic patients develop significant quantities of ovomucoid-specific IgG antibodies to linear and conformational epitopes whereas non-egg allergic individuals develop ovomucoid-specific IgG almost exclusively to conformational epitopes.

As noted above, elevated levels of food-specific IgG antibodies also are seen in disorders marked by inflammation of the gastrointestinal tract, e.g. Crohn's disease, ulcerative colitis, celiac disease, etc. (Sampson, H. A.: 1995 11(6), 548–553). It is believed that the elevated food-specific antibodies are secondary to increased gut permeability in these disorders and are pathogenic. In uncomplicated inflammatory bowel disorders, it is likely that these food-specific IgG antibodies are directed at conformational epitopes. However, in progressive, refractory bowel disease, food-specific IgG antibodies are believed to be directed at linear epitopes, indicating an abnormal immune response and unfavorable prognosis.

Figure 4A:
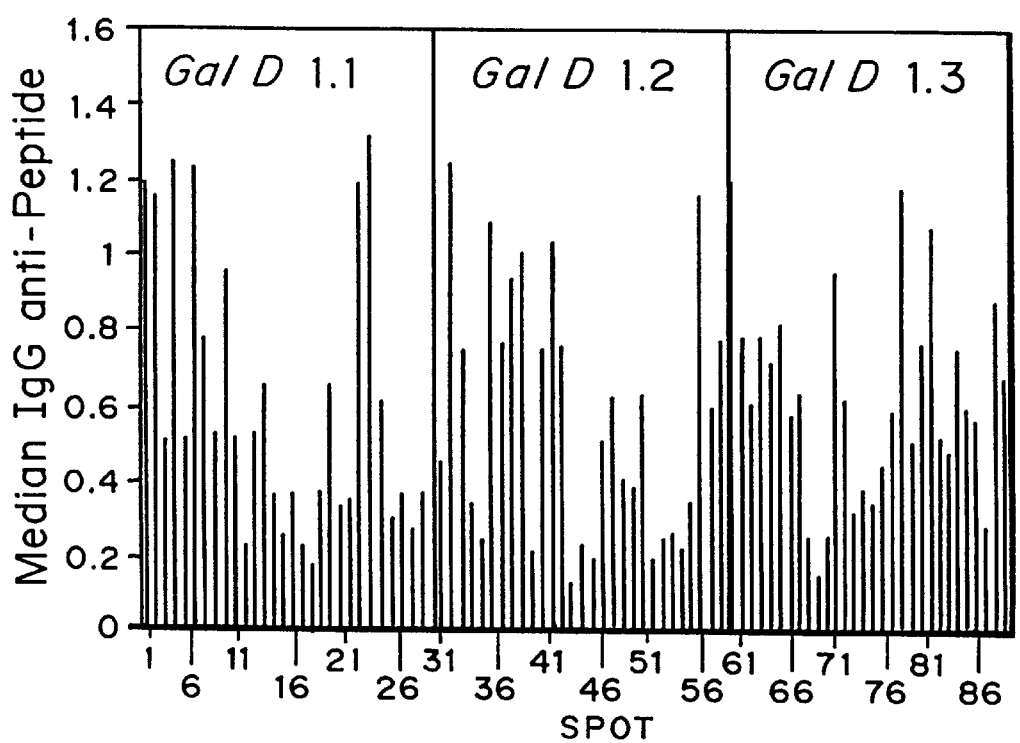
FIGS. 4a–e. Median cumulative SPOTs IgG Gal d 1 OD scores, egg-allergic patients (FIGS. 4a–4c) and non-egg-allergic controls:atopic dermatitis patients without egg allergy (FIG. 4d) and non-allergic normal controls (FIG. 4e).
Figure 4B:
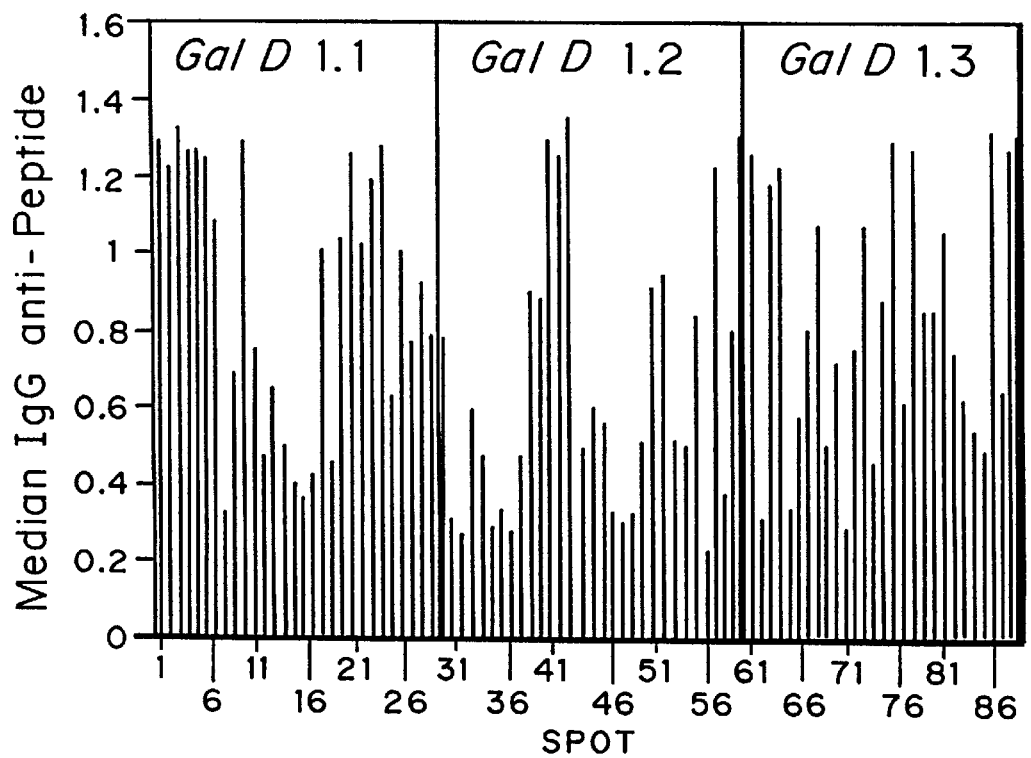
Figure 4C:
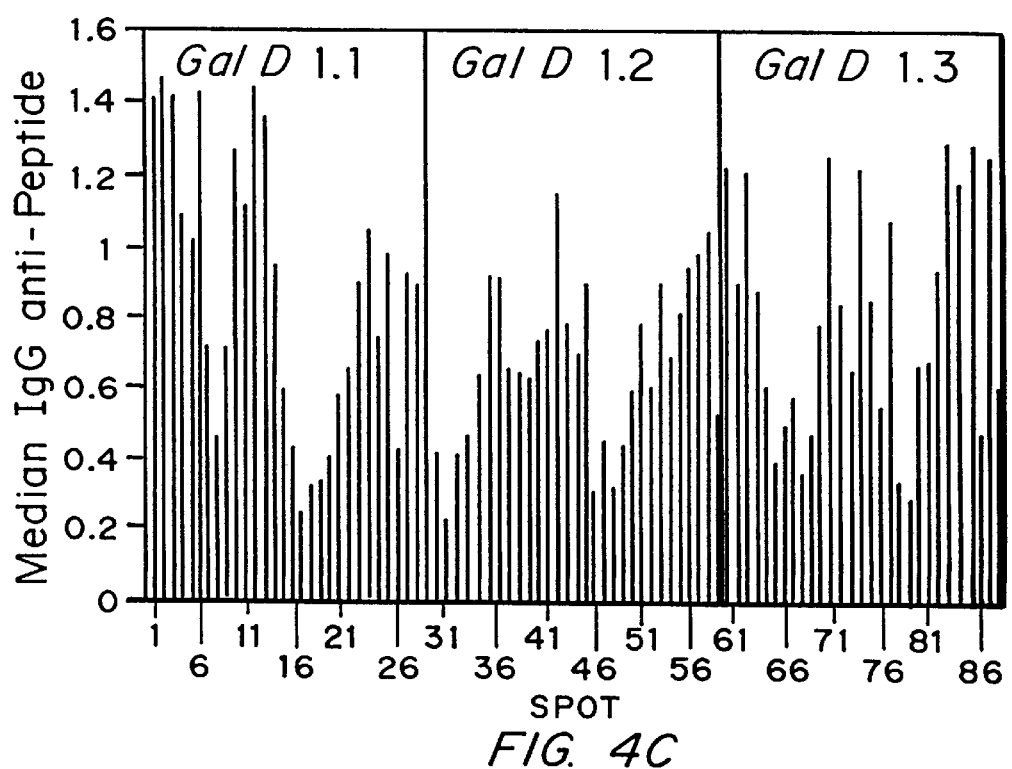
Figure 4D:
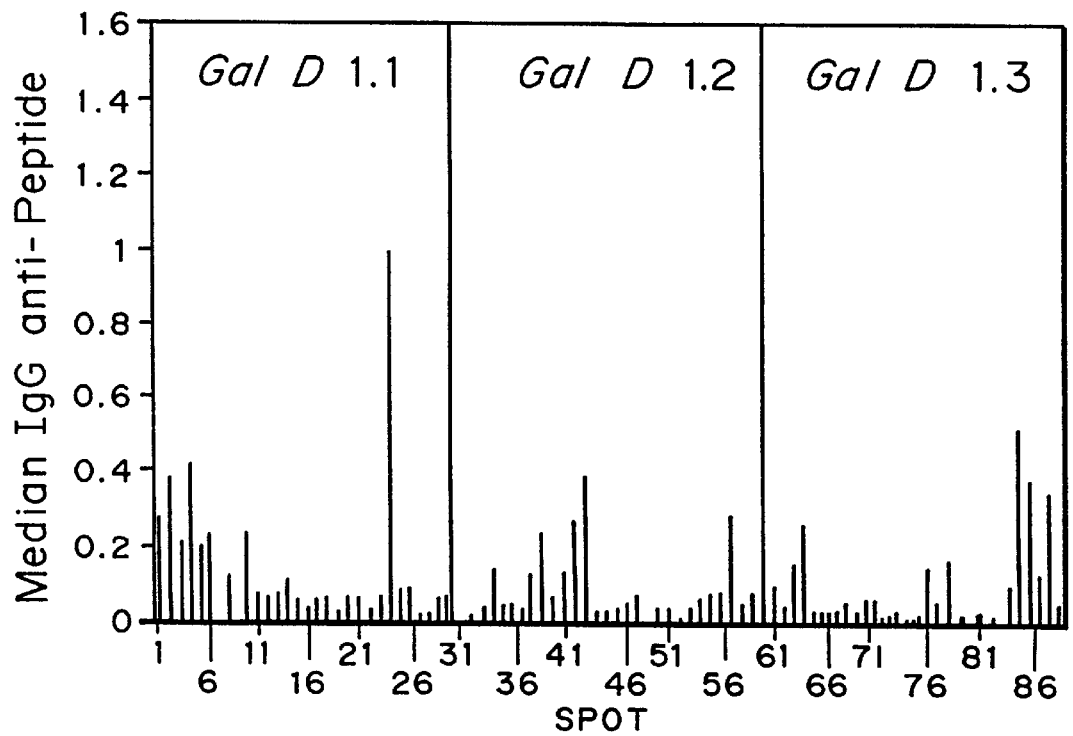
Figure 4E:
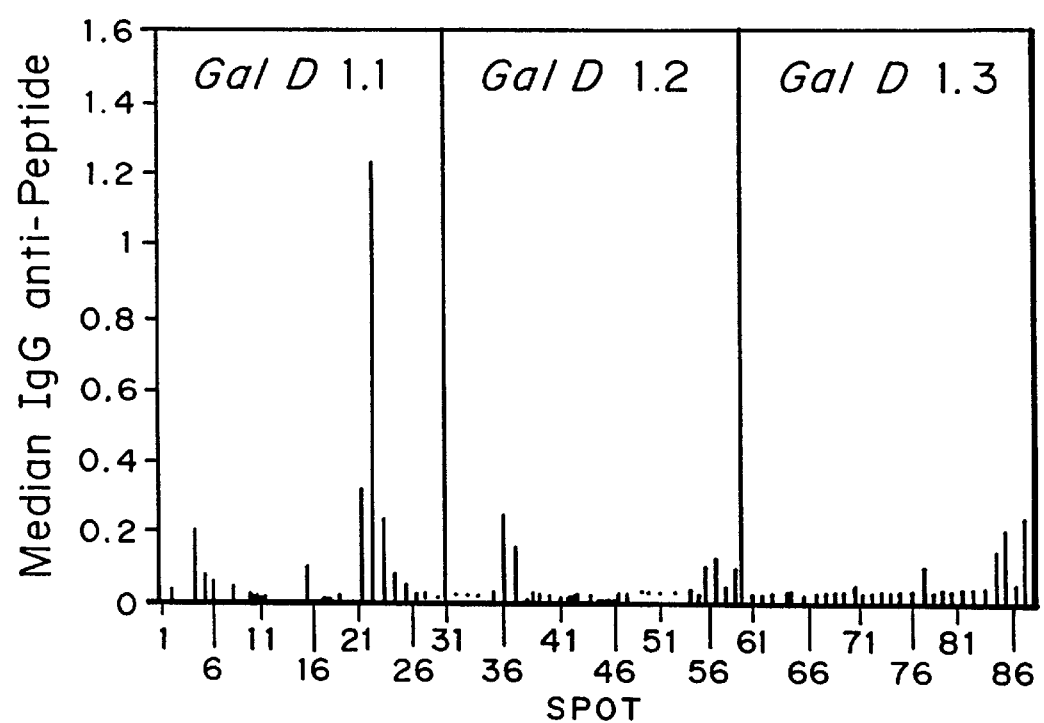
Figure 5B:
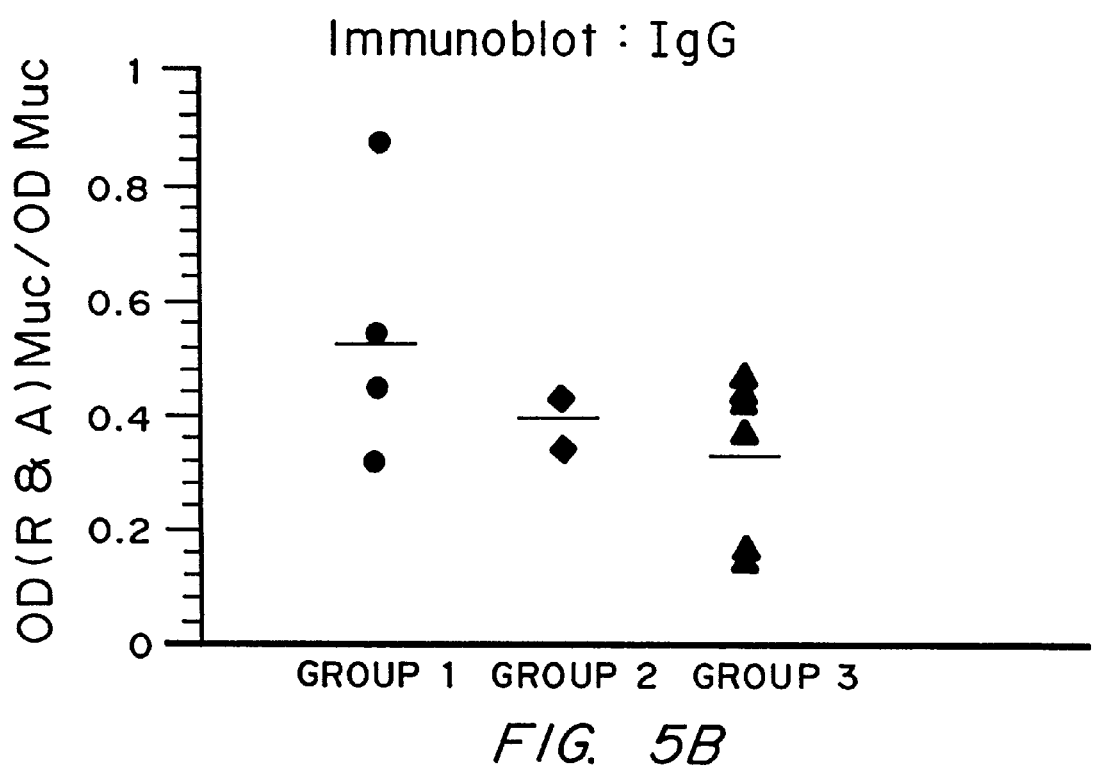

As shown by the example, when ovomucoid-specific IgG antibody binding to linear decapeptides were evaluated, significant differences were seen between egg-allergic patient groups and controls. The first patient group, which had the greatest amount of ovomucoid-specific IgE to the linear decapeptides, had significantly less ovomucoid-specific IgG antibody binding to the ovomucoid decapeptides than the second and third patient groups (FIGS. 4a–4c). As reflected in the median cumulative SPOTs IgG Gal d 1 OD scores, egg-allergic patients (FIGS. 4a–4c) had extensive IgG binding to epitopes in all three ovomucoid domains and significantly more ovomucoid-specific IgG antibodies to the SPOTs decapeptides than non-egg-allergic controls: atopic dermatitis patients without egg allergy (FIG. 4d) and non-allergic normal controls (FIG. 4e). The second (FIG. 4b) and third (FIG. 4c) groups of egg allergic patients had significantly more IgG antibody binding to the synthesized peptides than the first group (FIG. 4a). However, there was no significant difference in the percentage of ovomucoid-specific IgG binding to "linearized" ovomucoid compared to the native form (FIG. 5b). Control groups consisting of atopic dermatitis patients who were not allergic to egg and non-allergic normal controls had significant IgG antibodies to native ovomucoid but virtually no ovomucoid-specific IgG antibodies to the linear decapeptides (FIGS. 4d–4e). These results suggest a qualitative difference at the level of antigen processing between food allergic and non-allergic individuals in their immune response to ingested allergens.

It is therefore possible to screen for those individuals having inflammatory disorders which are likely to be characterized by progressive, refractory bowel disease, as compared to uncomplicated inflammatory bowel disorders. The methods and reagents are similar to those for determining the liklihood an individual will outgrow an allergy based on the relative proportions of IgE immunoreactive with linear versus conformational epitopes but examining the immunoreactivity of IgG to linear versus conformation epitopes.

The present invention will be further understood by reference to the following non-limiting example.

EXAMPLE

Screening of Patient Samples to Characterize the Immunoreactivity of Anti-egg IgE and IgG

METHODS AND MATERIALS

Abbreviations:
PBS—phosphate buffered saline
SDS-PAGE=sodium dodecylsulfate polyacrylamide gel electrophoresis

Patient Population

Seventeen children (median age: 4 yrs., range: 1–15 yrs.; 10 males, 7 females) presenting for evaluation of atopic dermatitis were diagnosed with egg hypersensitivity by double-blind placebo-controlled egg challenge, as described by Sampson, H. A. and C. C. McCaskill. 1985. *J Pediatr* 107:669–675; and Sampson, H. A. 1992. *Acta Derm Veneorol* (Stockh) Suppl. 176:34–37. Blood was obtained by venous puncture, and the sera separated and stored frozen at −20° C. until used in the study. Serum egg-specific IgE concentrations were determined utilizing the CAP-RAST FEIA™ system (Pharmacia Diagnostics; Uppsala, Sweden).

Preparation of Reduced and Alkylated Ovomucoid

Ovomucoid was reduced and alkylated by dissolving whole ovomucoid in PBS at a concentration of 50 mg/ml, as described by Cooke and Sampson. *J Immunol.* 1997.

SDS-Polyacrylamide Gel Electrophoresis

Proteins were separated by SDS-PAGE as previously published (Bernhisel-Broadbent, et al. 1989. *J Allergy Clin Immunol* 84:701–709). Protein sample concentrations were optimized to give equivalent signal when stained by amido black and analyzed by laser densitometry. The resolved proteins were subsequently transferred to nitrocellulose and then stained with amido black to look for total protein transfer, or blocked with PBS-TWEEN™ with 0.5% porcine gelatin for probing with patient sera.

Probing Immunoblots with Patient Sera

Patient sera were diluted 1:10 in PBS-Tween plus gelatin, incubated with immunoblots for 2 hours with gentle agitation at room temperature, and developed for IgE and IgG antibodies as previously described (Cooke and Sampson 1997). Immunoblots were developed with BCIP/NBT (SigmaFAST; Sigma Chemical, St Louis, Mo.) and scanned with a laser densitometer ULTRASCAN™ SL; Pharmacia Biotech, Piscataway, N.J.) to determine the amount of ovomucoid-specific antibody bound.

Screening for IgE and IgG Epitopes

In this study, the SPOTs™ membrane (Genosys Biosystems; The Woodlands, Tex.), a derivatised cellulose membrane was used to generate decapeptides in an 8×12 matrix of small circular spots. Using this method, 89 decapeptides representing the entire sequence of Gal d 1 were generated; peptides overlapped by 8 amino acids, e.g. peptide #1=Gal d 1 amino acids 1–10, peptide #2=Gal d 1 amino acids 3–12, peptide #3=Gal d 1 amino acids 5–14, etc.

Prior to screening the overlapping Gal d 1 peptides with patient sera, the SPOTs membrane was blocked with PBS (pH 7.2) containing 0.01% Tween 20, 0.5% porcine gelatin, and 1% human serum (from a donor with no detectable IgE to egg proteins). Individual patient sera were diluted 1:12 in PBS with 0.01% TWEEN™ 20 and 0.5% porcine gelatin (PBS-Tween+gel), incubated on a rocking platform at room temperature for 2 hours, and developed for IgE antibodies as previously described (Cooke and Sampson 1997). For detecting patient IgG antibodies, patient sera were diluted 1:10 in PBS-Tween+gel. Incubation times and washes were the same as for IgE antibody. The detecting antibody used was rabbit anti-human IgG-HRP conjugate (Dako Corp, Santa Barbara, Calif.). The membrane was developed with the ECL chemiluminescent HRP detection kit (Amersham, Arlington Heights, Ill.).

After developing the x-ray film, the optical density (OD) of each individual peptide spot was measured using a reflection densitometer (The Answer II MacBeth, Newburgh, N.Y.). The OD of each peptide spot was recorded as the difference between the actual peptide spot OD and the background film OD. Each of the 89 decapeptides was assigned a "cumulative SPOTs" IgE and IgG Gal d 1 OD score, which represented the sum of the ODs for each of the 89 Gal d 1 SPOT peptides for the 17 patients studied. Each patient received a "cumulative patient" IgE and IgG Gal d 1 OD score, which represented the sum of the ODs for all 89 Gal d 1 SPOT peptides for that patient.

The SPOTs membrane could be regenerated and re-probed 8 to 10 times. After rinsing the membrane thoroughly in deionized, distilled water, it was washed 3 times in 8 M urea containing 35 Mm SDS and 0.1% BME for 10 minutes each time to strip IgE or 30 minutes to strip IgG. The membrane was then washed three times (10 minute washes) in 50% ethanol and 10% acetic acid, twice (10 minute washes) in methanol, and then re-blocked for re-probing. Incubation of the membrane with the secondary antibody alone (anti-human IgE or IgG) following the stripping procedure in the absence of patient serum revealed no non-specific binding, indicating that the stripping procedure had successfully regenerated the SPOTs membrane.

Statistical Analysis

All analyses of data were performed with non-parametric tests, the paired, two-sample sign test and the Mann Whitney test.

RESULTS

Figure 1:
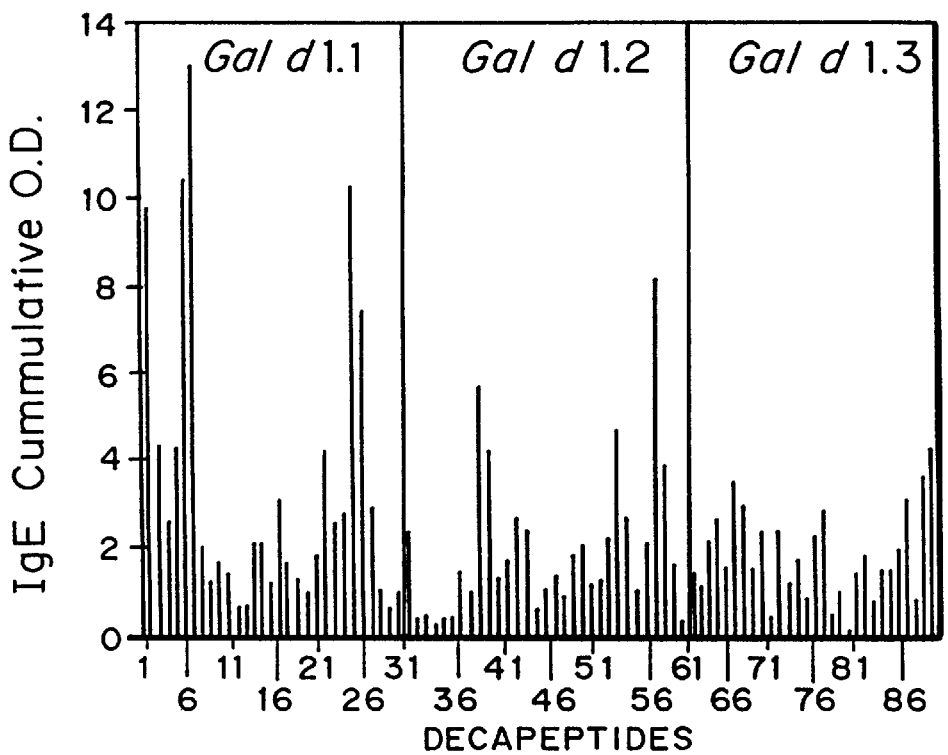
FIG. 1. Cumulative SPOTs IgE Gal d 1 OD scores for each of the 89 overlapping synthetic decapeptides generated on the SPOTs membrane. Scores reflect total binding of the 17 egg allergic patients studied.
Figure 2:
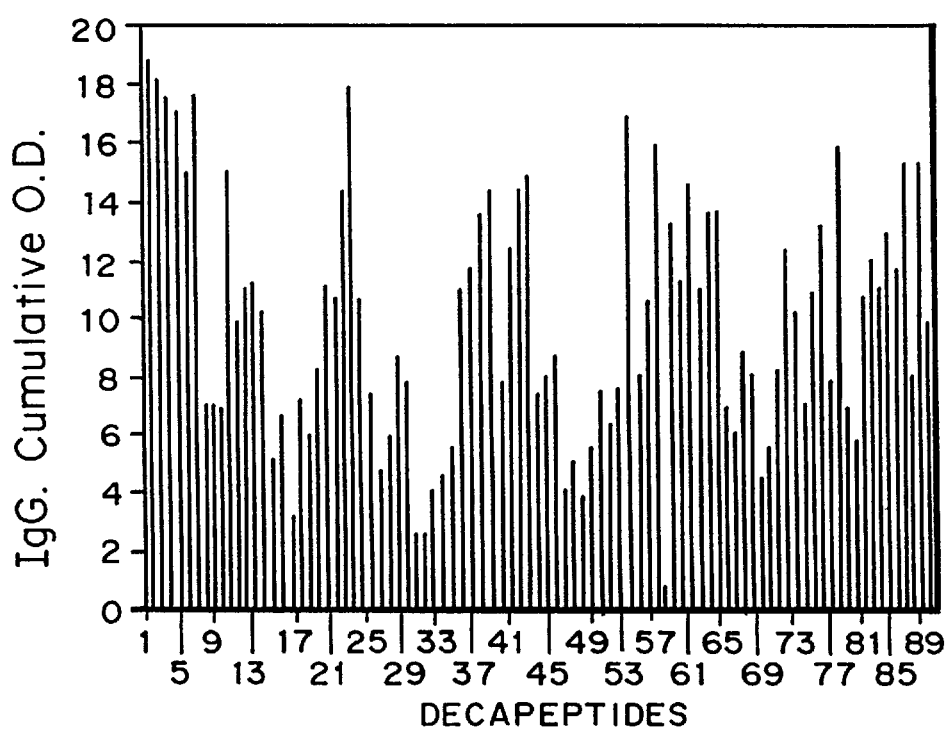
FIG. 2. Cumulative SPOTs IgG Gal d 1 OD scores for each of the 89 overlapping synthetic decapeptides generated on the SPOTs membrane. Scores reflect total binding of the 17 egg allergic patients studied.

Sera from 17 children with egg allergy confirmed by double-blind placebo-controlled food challenges were utilized in the study. All had markedly elevated serum egg-specific IgE; median—83 Kua/L; range—35 to greater than 100 kUA/L. Individual patients' sera were used to probe the SPOTs membrane for IgE and IgG peptide-specific antibodies. FIG. 1 depicts the cumulative SPOTs IgE Gal d 1 O.D. scores for each of 89 synthetic peptides. Peptides #1, #5, #6, #24, #25, and #57 were bound by IgE antibodies from greater than 50% of the patients, indicating that these peptides represent "major allergenic epitopes." These major allergenic epitopes, represent Gal d 1 amino acids 1–10 (peptide 1, AEVDCSRFPN)(SEQ ID NO:1), 9–20 (peptides 5 and 6, PNATDKEGKDVL)(SEQ ID NO:2), 47–58 (peptides 24 and 25, SIEFGTNISKEH)(SEQ ID NO:3), and 113–122 (eptide 57, VEQGASVDKR)(SEQ ID NO:4). Other synthetic peptides with significant IgE Gal d 1 SPOTs OD scores included peptides 2 (amino acids 3–12, VDCSRFPNAT)(SEQ ID NO:5), 4 (amino acids 7–16, RFPNATDKEG)(SEQ ID NO:6), 21 (amino acids 41–50, CLLCAYSIEF)(SEQ ID NO:7), 38 and 39 (amino acids 75–86, NTTSEDGKVMVL)(SEQ ID NO:8), 53 (amino acids 105–114, ECLLCAHKVE)(SEQ ID NO:9), and 89 (amino acids 177–186, TLTLSHFGKC)(SEQ ID NO:10). Most of these peptides were bound by IgE antibodies from 6 or more patients. FIG. 2 depicts the cumulative IgG Gal d 1 SPOTs O.D. scores for each of the 89 synthetic decapeptides. There was more extensive binding of IgG antibodies to the Gal d 1 synthetic peptides compared to the IgE binding.

When IgE antibody binding to the SPOTsmembranes; decapeptides for each patient were compared, three different patterns of peptide binding were seen: Group 1—IgE antibodies bound epitopes in two or more Gal d 1 domains, Group 2—IgE antibodies specific for peptides primarily in the first Gal d 1 domain, and Group 3—negligible IgE binding to any of the decapeptides on the SPOTs membrane. Although there were nosignificant differences (p>0.4) in the serum egg-specific IgE concentrations among the 3 patient groups (Group 1 (n=5)—80 kUA/L, Group 2 (n=5)—92 kUA/L, and Group 3 (n=7)—73 kUA/L), the median cumulative SPOTs IgE Gal d 1 OD scores for the three patient groups differed significantly. Group 1 patients had significantly more IgE binding (median cumulative OD=27.9) to the synthesized Gal d 1 decapeptides than either Group 2 (median cumulative OD=7.0; p<0.05) or Group 3 (median cumulative OD=2.7; p<0.01), and Group 2 had significantly more IgE binding to Gal d 1 peptides than Group 3 (p<0.05). The median IgE binding to individual decapeptides for each patient group is depicted in FIG. 3. Interestingly, patients in Groups 1 and 2 tended to be older with longer-standing egg allergy compared to patients in Group 3; median age 10 and 6 years, respectively, with all patients diagnosed within the first 2 years of life.

FIG. 4a–4e depict the median IgG binding to individual decapeptides for each of the 3 patient groups and 2 sets of controls. Significant differences in median cumulative patient IgG Gal d 1 OD scores ere seen among the three patient groups and controls: Group 1—52.4, Group 2—70.6, Group 3—69.8, non-food allergic atopic dermatitis controls (n=5)—9.6, non-allergic controls (n=5)—11.6. Group 1 patients had significantly less IgG antibody binding to Gal d 1 decapeptides than Groups 2 and 3 (p<0.01), whereas there was no significant difference between Groups 2 and 3 (p=0.4). The three egg allergic patient groups had significantly more IgG binding to the ovomucoid decapeptides than the two non-egg allergic control groups (p<0.01). The non-egg allergic atopic dermatitis patient controls and non-atopic controls showed similar (p=0.4), minimal IgG antibody binding to the 89 SPOTs decapeptides.

The lack of IgE binding to the synthesized peptides by Group 3 egg-allergic patients suggested that the majority of their ovomucoid-specific IgE antibodies recognized conformational epitopes. To examine this, IgE antibody binding to native and reduced and alkylated (linearized) ovomucoid was compared in the three patient groups. FIGS. 5a–b depict the ratios of IgE antibody binding (OD) to reduced and alkylated ovomucoid compared to IgE antibody binding to native ovomucoid. The ratio of ovomucoid-specific IgE and IgG antibodies to native and "linearized" (reduced and alkylated) ovomucoid were compared for each egg allergic patient group. Although IgE antibody concentrations to native ovomucoid were comparable for all groups, Group 1 patients, who were older with longstanding egg allergy, had significantly more IgE antibodies to linearized ovomucoid than Group 3 patients, who were younger (FIG. 5a). (FIG. 5a—medians: 52% vs. 22% for Groups 1 and 3, respectively, p<0.05). No significant differences in the ratio of IgG antibodies to linearized-native ovomucoid were seen among the egg-allergic patient groups (FIG. 5b).

Modifications and variations of the present invention will be obvious to those skilled in the art from the foregoing detailed description.

I claim:

1. A method of determining whether an individual will outgrow an allergy elicited by exposure to an inhaled or ingested allergen, comprising
   a) obtaining a sample of antibodies from the individual with an allergy,
   b) contacting the sample with a plurality of linear and conformational epitopes, wherein the epitopes are derived from an allergen selected from the group consisting of natural purified allergen, recombinant allergen, reduced and alkylated allergen, proteolytic fragments of the allergen, and synthetic peptides of between four and 40 amino acids in length,
   c) screening the immunoreactivity of IgE antibody that binds to the linear or conformational epitopes, and
   d) determining that the individual with IgE anitibody that are more reactive with conformational epitopes relative to linear epitopes will outgrow the allergy.

2. The method of claim 1 wherein the conformational epitopes are selected from the group consisting of natural purified allergen and proteolytic fragments of natural purified allergen and wherein the linear epitopes are selected from the group consisting of allergen and synthetic peptides of between four and 40 amino acids in length.

3. The method of claim 2 wherein the epitopes are derived from allergens selected from the group consisting of food and pollens.

4. The method of claim 3 wherein the allergen is a food protein.

5. The method of claim 4 wherein the epitopes are derived from allergens selected from the group consisting of peanut, egg, tree nuts, milk, fish, and shell fish.

* * * * *

SEQUENCE LISTING

<160> NUMBER OF SEQ ID NOS: 10

<210> SEQ ID NO 1
<211> LENGTH: 10
<212> TYPE: PRT
<213> ORGANISM: Artificial Sequence
<220> FEATURE:

-continued

<223> OTHER INFORMATION: Description of Artificial Sequence: peptide

<400> SEQUENCE: 1

Ala Glu Val Asp Cys Ser Arg Phe Pro Asn
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: peptide

<400> SEQUENCE: 2

Pro Asn Ala Thr Asp Lys Glu Gly Lys Asp Val Leu
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: peptide

<400> SEQUENCE: 3

Ser Ile Glu Phe Gly Thr Asn Ile Ser Lys Glu His
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: peptide

<400> SEQUENCE: 4

Val Glu Gln Gly Ala Ser Val Asp Lys Arg
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: peptide

<400> SEQUENCE: 5

Val Asp Cys Ser Arg Phe Pro Asn Ala Thr
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: peptide

<400> SEQUENCE: 6

Arg Phe Pro Asn Ala Thr Asp Lys Glu Gly
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: peptide

```
<400> SEQUENCE: 7

Cys Leu Leu Cys Ala Tyr Ser Ile Glu Phe
  1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: peptide

<400> SEQUENCE: 8

Asn Thr Thr Ser Glu Asp Gly Lys Val Met Val Leu
  1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: peptide

<400> SEQUENCE: 9

Glu Cys Leu Leu Cys Ala His Lys Val Glu
  1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: peptide

<400> SEQUENCE: 10

Thr Leu Thr Leu Ser His Phe Gly Lys Cys
  1               5                  10
```